United States Patent
Kozlowski

(10) Patent No.: US 8,080,027 B2
(45) Date of Patent: Dec. 20, 2011

(54) SURGICAL KNIFE BLADE WITH HOLLOW BEVEL

(75) Inventor: Martin J. Kozlowski, Kutztown, PA (US)

(73) Assignee: Surgical Specialties Corporation

( * ) Notice: Subject to any disclaimer, the term of this patent is extended or adjusted under 35 U.S.C. 154(b) by 443 days.

(21) Appl. No.: 10/942,437

(22) Filed: Sep. 15, 2004

(65) Prior Publication Data
US 2006/0058824 A1 Mar. 16, 2006

(51) Int. Cl.
*A61B 17/32* (2006.01)
(52) U.S. Cl. ............... 606/166; 606/170; 30/346.55
(58) Field of Classification Search ............ 30/123.7, 30/123, 32, 49, 346, 346.55, 346.56, 346.57, 30/353, 355, 357; 606/107, 166–183, 184, 606/185; 604/164.01, 164.06
See application file for complete search history.

(56) References Cited

U.S. PATENT DOCUMENTS

| | | | |
|---|---|---|---|
| 4,766,896 A * | 8/1988 | Pao | 606/170 |
| 5,207,696 A | 5/1993 | Matwijcow | |
| 5,217,476 A * | 6/1993 | Wishinsky | 606/167 |
| 5,217,477 A * | 6/1993 | Lager | 606/167 |
| 5,370,652 A * | 12/1994 | Kellan | 606/166 |
| D370,532 S * | 6/1996 | Epstein et al. | D24/146 |
| 6,063,099 A * | 5/2000 | Danks et al. | 606/185 |
| 6,139,559 A | 10/2000 | Nordan et al. | |
| 6,264,668 B1 * | 7/2001 | Prywes | 606/167 |
| 6,743,128 B2 * | 6/2004 | Liechty, II | 473/583 |
| 2001/0029386 A1 | 10/2001 | Matsutani et al. | |
| 2004/0133224 A1 | 7/2004 | Scheller et al. | |

OTHER PUBLICATIONS

Website http://www.surgicalspecialtles.com/onlinecatalog/ophthalmic.php, Title Page of Online Catalog, Sep. 1, 2004, 1 pg.
Website http://www.surgicalspecialties.com/onlinecatalog/catalog_knives.php?market=Ophthalmic..., Surgical Specialties Corporation—Online Catalog, "Knives—Ophthalmic / Blade and Tip Handles", Sep. 1, 2004, 1 pg.
Website http://www.surgicalspecialties.com/onlinecatalog/catalog_knives.php?market=Ophthalmic..., Surgical Specialties Corporation—Online Catalog, "Knives—Ophthalmic /Clear Corneal Knives, Double Bevel, Parallel Sides", Sep. 1, 2004, 1 pg.
Website http://www.surgicalspecialties.com/onlinecatalog/catalog_knives.php?rnarket=Ophthalmic..., Surgical Specialties Corporation—Online Catalog, "Knives—Ophthalmic / ClearTrap Trapezoid, Clear Corneal/Implant Knife", Sep. 1, 2004, 1 pg.
Website http://www.surgicalspecialties.com/onlinecatalog/catalog_knives.php?market=Ophthalmic..., Surgical Specialties Corporation—Online Catalog, "Knives—Ophthalmic / Implant Knives", Sep. 1, 2004, 1 pg.

(Continued)

*Primary Examiner* — Kathleen Sonnett
(74) *Attorney, Agent, or Firm* — Angiotech

(57) ABSTRACT

A surgical knife blade for forming an incision in bodily tissue including a body having a cutting edge terminating at a distal tip, the cutting edge including opposing cutting edge segments extending distally to meet at the tip, the cutting edge being configured by blending a first and second radii. The first radius is concave and the second radius is convex, the first and second radii meet at a juncture which forms a smooth tangential connection, whereby the blended radii form a hollow design and wherein when the body is moved in a cutting direction transverse to the tissue to cause the tip to enter the tissue, less force is required to penetrate the bodily tissue and greater control is provided.

10 Claims, 2 Drawing Sheets

OTHER PUBLICATIONS

Website http://www.surgicalspecialties.com/onlinecatalog/catalog_knives.php?market=Ophthalmic..., Surgical Specialties Corporation—Online Catalog, "Knives—Ophthalmic / Pilot Tip Implant Knives", Sep. 1, 2004, 1 pg.

Website http://www.surgicalspecialties.com/onlinecatalog/catalog_knives.php?market=Ophthalmic..., Surgical Specialties Corporation—Online Catalog, "Knives—Ophthalmic / Precision Depth Knives", Sep. 1, 2004, 1 pg.

Website http://www.surgicalspecialties.com/onlinecatalog/catalog_knives.php?market=Ophthalmic..., Surgical Specialties Corporation—Online Catalog, "Knives—Ophthalmic / Sharptome Crescent Design Knives", Sep. 1, 2004, 1 pg.

Website http://www.surgicalspecialties.com/onlinecatalog/catalog_knives.php?market=Ophthalmic..., Surgical Specialties Corporation—Online Catalog, "Knives—Ophthalmic / Slit Knives", Sep. 1, 2004, 1 pg.

Website http://www.surgicalspecialties.com/onlinecatalog/catalog_knives.php?market=Ophthalmic..., Surgical Specialties Corporation—Online Catalog, "Knives—Ophthalmic / Slit Knives—Bevel Up", Sep. 1, 2004, 1 pg.

Website http://www.surgicalspecialties.com/onlinecatalog/catalog_knives.php?market=Ophthalmic..., Surgical Specialties Corporation—Online Catalog, "Knives—Ophthalmic / Slit Knives—Double Bevel", Sep. 1, 2004, 1 pg.

Website http://www.surgicalspecialties.com/onlinecatalog/catalog_knives.php?market=Ophthalmic..., Surgical Specialties Corporation—Online Catalog, "Knives—Ophthalmic / Slit Knives—Parallel Sides", Sep. 1, 2004, 1 pg.

Website http://www.surgicalspecialties.com/onlinecatalog/catalog_knives.php?market=Ophthalmic..., Surgical Specialties Corporation—Online Catalog, "Knives—Ophthalmic / Specialty Knives", Sep. 1, 2004, 1 pg.

Website http://www.surgicalspecialties.com/onlinecatalog/catalog_knives.php?market=Ophthalmic..., Surgical Specialties Corporation—Online Catalog, "Knives—Ophthalmic / Spoon Knives", Sep. 1, 2004, 1 pg.

Website http://www.surgicalspecialties.com/onlinecatalog/catalog_knives.php?market=Ophthalmic..., Surgical Specialties Corporation—Online Catalog, "Knives—Ophthalmic / Stab Knives", Sep. 1, 2004, 1 pg.

Website http://www.surgicalspecialties.com/onlinecatalog/catalog_knives.php?market=Ophthalmic..., Surgical Specialties Corporation—Online Catalog, "Knives—Ophthalmic / Sub-2mm Series Knives", Sep. 1, 2004, 1 pg.

Website http://www.surgicalspecialties.com/onlinecatalog/catalog_knives.php?market=Ophthalmic..., Surgical Specialties Corporation—Online Catalog, "Knives—Ophthalmic / Vitrectomy Knives", Sep. 1, 2004, 1 pg.

Website http://www.milab.ru/800/knives_e.html, MicroInstrument LABoratory—Knives for the opthalmology—The MicroHand standart instrument, Sep. 1, 2004, 3 pgs.

Website http://www.pricon.org/opthalmic/showcat.php?catid=25, Microsurgical Instruments: JC0001: Lasik Speculum / Facet—Free Crescent Knife, Sep. 1, 2004, 2 pgs.

Website http://www.surgicalspecialties.com/news/viewnewsdetail.php?newsid=33, Surgical Specialties Corporation, "In the News—Learn about our Infinite Edge Technology", Sep. 1, 2004, 2 pgs.

* cited by examiner

SURGICAL KNIFE BLADE WITH HOLLOW BEVEL

FIELD OF THE INVENTION

The invention relates, generally, to surgical knife blades and, more particularly, to a surgical knife blade for precisely creating and forming incisions in bodily tissue.

BACKGROUND OF THE INVENTION

Many surgical procedures require the use of surgical knives for forming incisions in bodily tissue to provide access to a body cavity or internal operative site. Most surgical knives include a handle having a cutting blade mounted on a distal end thereof for being inserted in tissue to produce an incision. The cutting blades on surgical knives are usually of minimal thickness to penetrate tissue easily with minimal trauma such that the incisions can be closed without excessive stretching of surrounding tissue while promoting rapid healing with minimal scarring. The cutting blades on surgical knives are typically available in a variety of sizes and have a maximum width between opposing lateral sides of the blade, the blades being tapered to extend longitudinally in a distal direction from the area of maximum width to a sharp tip, or point, facilitating insertion of the blade in tissue. Accordingly, the lateral sides of the blades are configured to extend distally with a desired taper, and the exact configuration for the taper varies dependent upon the type of incision to be produced for a specific operative procedure or the desires of individual surgeons. When forming relatively long incisions, a blade is inserted in the bodily tissue in the manner of a plunge cut; and, once the tip or point has penetrated the tissue to the required depth for the operative procedure being performed, the blade is moved through the tissue in line with the lateral sides until an incision is produced having a length sufficient to provide access for the operative procedure. The length of the incision can be several times greater than the width of the blade; and, frequently, deviance of actual incision length from an optimal incision length for the operative procedure is not medically significant. However, many operative procedures require that the lengths of incisions be precisely formed to avoid damage to surrounding tissue and organs as well as other adverse complications of surgery.

In cataract surgery and other microsurgical procedures, the lengths of incisions must be very small; and, when forming incisions that are small in length, a knife blade having a known size, or maximum width, as close as possible to the length of incision desired is usually inserted in tissue in a direction normal thereto in the manner of a plunge cut to form an incision in the tissue surface extending lengthwise between the lateral sides of the blade. In other words, an incision having an end-to-end length corresponding to the known width of the blade is formed in the tissue surface when the blade is inserted deep enough to penetrate the tissue surface to the known blade width. Because individual knife blades are conventionally sized to reflect a single, known blade width, an individual blade can precisely form only a single incision of a predetermined width. The lengths of incisions that can be precisely formed utilizing conventional surgical knife blades are limited due to the knife blades being manufactured in a limited number of sizes, or widths. Consequently, in many cases the actual lengths of incisions made with surgical knife blades must be subjectively estimated during incision formation to approximate the optimal incision length, and the actual length of an incision thusly formed is not known absent the use of extraneous measuring devices.

In cataract surgery, the length of an incision made in the sclera or adjacent tissue must be large enough to provide access for lens removal yet no larger than necessary to avoid distortion of the curvature of the eye, or astigmatism, when the incision is closed. In lens removal and replacement surgery of the eye, an incision is made in the eye to be only large enough in length to permit removal of the natural lens due to a blindness causing condition, such as cataract. The optimal length for the incision is very small, i.e. approximately 3 mm, and a surgical knife blade having a known size, close to 3 mm is selected for forming the incision or a thin blade is used with a lateral cutting movement. With a surgeon manipulating the blade via the handle thereon, the tip of the blade is utilized to initially penetrate the sclera, and the blade is inserted while calipers set to 3 mm are held adjacent the incision to compare actual incision length with the calibrated length. If the length of the incision is smaller than desired, the blade is manipulated and incision length measurements are repeated until the proper length incision has been obtained. Once the incision is determined to be accurately formed, the blade is removed, and a surgical instrument is introduced through the incision to remove the natural lens in accordance with a procedure selected for lens removal, such as phacoemulsification. After the natural lens has been removed, a lens implant selected to replace the natural lens is inserted through the incision; and, in most cases, the initial incision must be lengthened to accommodate the implant. Usually, the length of the initial incision must be enlarged to at least 4 mm and, more typically, to approximately 5 mm. A second blade with a known size, as close as possible to the minimum length incision required to accommodate the implant is inserted in the initial incision in a direction normal to the sclera or the incision is enlarged with a smaller blade. As with the initial incision, calipers set to the desired length for the final incision are employed to compare the enlarged incision length with the desired length. Once the desired incision length if formed, the implant is inserted through the incision into the eye.

A problem associated with prior art blades relates to the initial penetration of the knife in the body tissue. For example, the force required to penetrate the tissue, even for ocular tissue, causes unnecessary trauma and reduces the surgeons control of the architecture of the incision while minimizing the chance of driving the keratome too deep.

SUMMARY OF THE INVENTION

It is an object of the present invention to overcome the aforementioned disadvantages of prior art surgical knife blades.

It is a further object of the present invention to provide a surgical knife blade for precisely creating and forming incisions in bodily tissue.

An additional object of the present invention is to provide a surgical knife blade to significantly reduce the force required to penetrate bodily tissue, such as ocular tissue.

The advantage of the present invention is a significantly reduced force to penetrate ocular tissue. This results in less wound trauma and improves surgical outcome. With less force required to make the cut the surgeon has better control of the architecture of the incision while minimizing the chance of driving the keratome to deep.

The present invention provides a surgical knife blade for forming an incision in bodily tissue comprising a body having a cutting edge terminating at a distal tip, said cutting edge including opposing cutting edge segments extending distally to meet at said tip, said cutting edge being configured by blending a first and second radii. The first radius is concave and the second radius is convex, the first and second radii meet at a juncture which forms a smooth tangential connection, whereby the blended radii form a hollow design and wherein when said body is moved in a cutting direction transverse to the tissue to cause said tip to enter the tissue, less force is required to penetrate the bodily tissue and greater control is provided.

The present invention also provides a surgical ophthalmic knife for forming an incision in ocular tissue, comprising an elongated handle having proximal end and a distal end, and a blade body connected to the distal end of the handle, the blade body having a cutting edge terminating at a distal tip, said cutting edge including opposing cutting edge segments extending distally to meet at said tip, said cutting edge being configured by blending a first and second radii. The first radius is concave and the second radius is convex, the first and second radii meet at a juncture which forms a smooth tangential connection, whereby the blended radii form a hollow design and wherein when said body is moved in a cutting direction transverse to the tissue to cause said tip to enter the tissue, less force is required to penetrate the bodily tissue and greater control is provided.

DETAILED DESCRIPTION OF THE INVENTION

Figure 1:
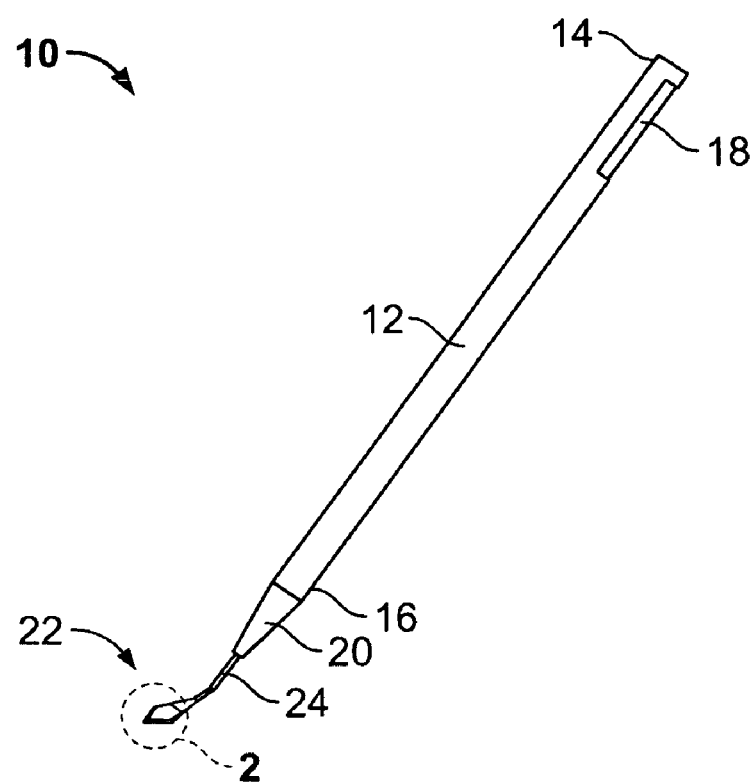
FIG. 1 is a perspective view of a surgical knife according to the present invention.

FIG. 1 shows a surgical knife 10 which includes an elongated handle 12 having a proximal end 14 and a distal end 16. The proximal end 14 includes a notched portion 18 and the distal end 16 includes a tapered section 20. A blade 22 is connected to the distal end 16 of the handle 12 via a stem 24.

Figure 2:
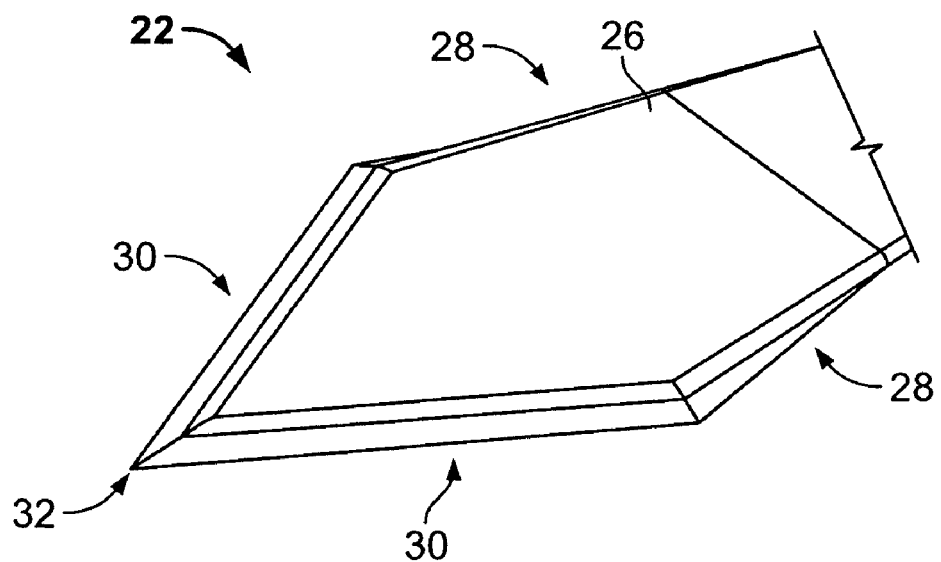
FIG. 2 is an enlarged view of a portion of the knife blade shown in FIG. 1 in accordance with the present invention.

FIG. 2 shows an enlarged view of a portion of the blade 22 of FIG. 1. The blade 22 includes a blade body 26 having opposing rear cutting edges 28 that extend in a diverging manner from one another away from the stem 24. The blade body 26 further includes opposing front cutting edges 30 which extend from the opposing rear cutting edge 28 and toward one another where they meet at a distal tip 32.

Figure 3:
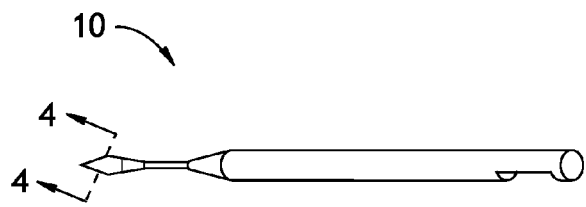
FIG. 3 is a top plan view of the surgical knife of FIG. 1
Figure 4:
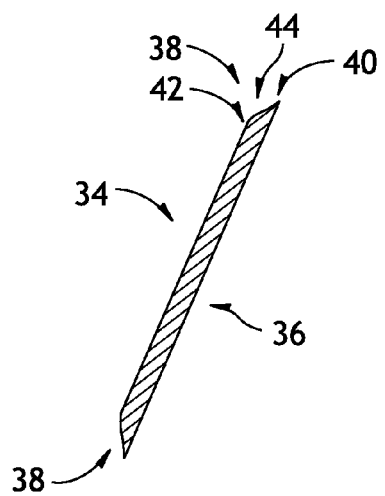
FIG. 4 is a cross sectional view of the surgical knife blade taken along line 4-4 of FIG. 3, according to the present invention.

FIG. 3 shows a top plan view of the surgical knife of FIG. 1. FIG. 4 shows a cross section of the blade body 26 taken along line 4-4 of FIG. 3. FIG. 4 shows that the blade body includes a top side 34 and a bottom side 36. FIG. 4 also shows that the cutting edge 38 includes a concave radius 40 extending from the bottom side 36, and a convex radius 42 extending from the top side 34. The concave radius 40 and the convex radius 42 meet at a juncture 44 which forms a smooth tangential connection.

Figure 5:
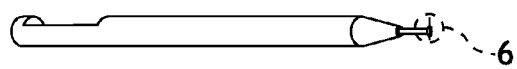
FIG. 5 is a front plan view of the surgical knife of FIG. 1 in accordance with the present invention.
Figure 6:
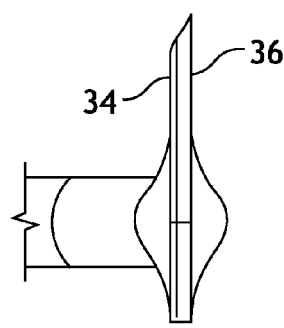
FIG. 6 is an enlarged view of a portion of the knife blade shown in FIG. 5 in accordance with the present invention

FIG. 5 shows a front plan view of the surgical knife 10 of FIG. 1. FIG. 6 shows an enlarged view of a portion of the surgical knife 10 of FIG. 5. FIG. 6 shows that the concave radius 40 extends between the top side 34 and bottom side 36 a distance which is longer than the respective distance of the convex radius 42.

Inasmuch as the present invention is subject to many variations, modifications and changes in detail, the subject matter discussed above and shown in the accompanying drawings is intended to be illustrative only and not to be taken in a limiting sense.

What is claimed:

1. A surgical ophthalmic knife blade for forming an incision in ocular tissue comprising:
   an ocular surgical blade body extending in a first plane and defining a top planar side and a bottom planar side, wherein the top planar side and the bottom planar side each extend in a respective plane substantially parallel to the first plane, the blade body comprising two opposing cutting edge segments, the two cutting edge segments extending from a tip, each of said two cutting edge segments being configured by blending a first and a second portion along the cutting edge segment, the first portion is concave and the second portion is convex, the first and second portions meet at a juncture which forms a smooth connection, wherein one of the first and second portion extends from the bottom planar side of the blade body, and the other of the first and second portion extends from the top planar side of the blade body, whereby the first and second portions form a hollow design, whereby significantly reduced force is required to penetrate the ocular tissue, resulting in less wound trauma.

2. A surgical ophthalmic knife blade as recited in claim 1 wherein each of said opposing cutting edge segments includes a front cutting edge segment extending from the tip and a rear cutting edge segments extending from the front cutting edge segment.

3. A surgical ophthalmic knife blade as recited in claim 1 wherein each of the opposing cutting edge segments extend in a linear direction.

4. A surgical ophthalmic knife blade as recited in claim 1 wherein the first portion extends from the bottom planar side of the blade body, and the second portion extends from the top planar side of the blade body.

5. A surgical ophthalmic knife blade as recited in claim 4 wherein the first portion extends between the top and bottom planar sides a longer distance than the second portion.

6. A surgical ophthalmic knife for forming an incision in ocular tissue, comprising:
   an elongated ocular surgical knife handle adapted to be held by a physician during ocular surgery, the handle having a proximal end and a distal end, wherein the handle has a longitudinal axis extending from the proximal end to the distal end; and
   an ocular surgical blade body extending in a first plane and connected to the distal end of the handle, said blade body includes a top planar side and a bottom planar side, wherein the top planar side and the bottom planar side each extend in a respective plane substantially parallel to the first plane, the blade body having a cutting edge including opposing cutting edge segments extending distally and converging at a tip, each of said cutting edge segments defined by a lower portion adjacent to and extending from the bottom planar side in a concave manner in a direction toward the top planar side, and an upper portion adjacent to and extending from the top planar side in a convex manner in a direction towards the bottom planar side, the lower portion extends a majority of a distance between the top planar side and the bottom planar side, each of said cutting edge segments being further configured by blending the lower and upper portions along the cutting edge segment, wherein the lower portion and the upper portion meet at a juncture which forms a smooth connection, whereby the upper and lower portions form a hollow design, whereby significantly reduced force is required to penetrate the ocular tissue, resulting in less wound trauma.

7. A surgical ophthalmic knife as recited in claim 6 wherein each of said opposing cutting edge segments includes a front cutting edge segment adjacent to the tip, and a rear cutting edge segment adjacent to the front cutting edge segment.

8. A surgical ophthalmic knife as recited in claim 6 wherein each of the opposing cutting edge segments extends in a linear direction.

9. A surgical ophthalmic knife blade for forming an incision in ocular tissue comprising:

an ocular surgical blade body extending in a first plane and defining a top planar side and a bottom planar side, wherein the top planar side and the bottom planar side each extend in a respective plane substantially parallel to the first plane, the blade body having a cutting edge including opposing cutting edge segments extending distally to meet at a tip;

each of said cutting edge segments being configured by blending a first and second portion, the first portion having a curvature and the second portion having a curvature different from the curvature of the first portion, the first and second portions meeting at a juncture which forms a smooth connection, and wherein one of the first and second portions extends from the bottom planar side of the blade body, and the other of the first and second portions extends from the top planar side of the blade body, whereby the first and second portions form a hollow design, whereby significantly reduced force is required to penetrate the ocular tissue, resulting in less wound trauma.

10. A surgical ophthalmic knife for forming an incision in ocular tissue, comprising:

an elongated ocular surgical knife handle adapted to be held by a physician during ocular surgery, the handle having a proximal end and a distal end, wherein the handle has a longitudinal axis extending from the proximal end to the distal end; and an ocular surgical blade body extending in a first plane and connected to the distal end of the handle, said blade body has a top planar side and a bottom planar side, wherein the top planar side and the bottom planar side each extend in a respective plane substantially parallel to the first plane, the blade body having a cutting edge terminating at a distal tip, said cutting edge including opposing cutting edge segments extending distally to meet at said tip, each of said cutting edge segments being configured by blending a first and second portion along the cutting edge segment, the first portion is concave and the second portion is convex, the first and second portions meet at a juncture which forms a smooth connection, and wherein one of the first and second portions extends from the bottom planar side of the blade body, and the other of the first and second portions extends from the top planar side of the blade body, whereby the first and second portions form a hollow design, whereby significantly reduced force is required to penetrate the ocular tissue, resulting in less wound trauma.

* * * * *